United States Patent [19]
Bandman et al.

[11] Patent Number: 5,919,655
[45] Date of Patent: Jul. 6, 1999

[54] HUMAN PHOSPHOLEMMAN HOMOLOG

[75] Inventors: Olga Bandman; Jennifer L. Hillman, both of Mountain View, Calif.

[73] Assignee: Incyte Pharmaceuticals, Inc., Palo Alto, Calif.

[21] Appl. No.: 08/738,127

[22] Filed: Oct. 25, 1996

[51] Int. Cl.$^6$ ........................ C07H 21/04; C12N 15/12; C12N 15/63

[52] U.S. Cl. ................ 435/69.1; 536/23.1; 536/24.3; 435/320.1; 435/325; 435/252.3; 435/172.3

[58] Field of Search .................................. 536/23.5, 24.3, 536/23.1; 435/6, 320.1, 325, 252.3, 69.1, 172.3

[56] References Cited

PUBLICATIONS

Gen Bank Record R72515, Definition: yj90f09.r1 *Homo sapiens* cDNA clone 156041 5′ Similar to SP:A 40533, A40533 cAMP–dependent Protein Kinase Major Membrane Substrate Processor, 1995.

Palmer, C.J., et al., "Purification and Complete Sequence Determination of the Major Plasma Membrane Substrate for cAMP–dependent Protein Kinase and Protein Kinase C in Myocardium" *J. Biol. Chem.*, 266:11126–11130 (1991).

Moorman, J.R., et al., "Phospolemman Expression Induces a Hyperpolarization–activated Chloride Current in Xenopus Oocytes" *J. Biol. Chem.*, 267:14551–14554 (1992).

Walaas, S.I., et al., "Protein kinase C and cyclic AMP–dependent protein kinase phosphorylate phospholemman, an insulin and adrenaline–regulated membrane phosphoprotein, at specific sites in the carboxy terminal domain" *Biochem. J.*, 304:635–640 (1994).

Lindemann, J.P., "α–Adrenergic Stimulation of Sarcolemmmal Protein Phosphorylation and Slow Responses in Intact Myocardium" *J. Biol. Chem.*, 261:4860–4867 (1986).

Moorman, J.R., "Unitary anion currents through phospholemman channel molecules" *Nature*, 377:737–740 (1995).

Morrison, B.W., et al., "neu1 and ras initiate murine mammary tumors that share genetic markers generally absent in c–myc and int–2–initiated tumors" *Oncogene*, 9:3417–3426 (1994).

Morrison, B.W., "Mat–8, a Novel Phospholemman–like Protein Expressed in Human Breast Tumors, Induces a Chloride Conductance in *Xenopus Oocytes*" *J. Biol. Chem.*, 270:2176–2182 (1995).

Attali, B., et al., "A corticosteroid–induced gene expressing an 'IsK–like' K+ channel activity in Xenopus oocytes" *Proc. Natl. Acad. Sci.*, 92:6092–6096 (1995).

Takumi, T., et al., "Cloning of a Membrane Protein That Induces a Slow Voltage–Gated Potassium Current" *Science*, 242:1042–1045 (1988).

Attali, B., et al., "The protein IsK is a dual activator of K+ and Cl− channels" *Nature*, 365:850–852 (1993).

Ben–Efraim, I., et al., "Cytoplasmic and Extracellular IsK Peptides Activate Endogenous K+ and Cl− Channels in Xenopus Oocytes" *J. Biol. Chem.*, 271:8768–8771 (1996).

Mercer, R.W., et al., "Molecular Cloning and Immunological Characterization of the γ Polypeptides, a Small Protein Associated with the Na, K–ATPase" *J. Cell. Biol.*, 121;579–586 (1993).

*Primary Examiner*—John Ulm
*Assistant Examiner*—Nirmal S. Basi
*Attorney, Agent, or Firm*—Leanne C. Price; Incyte Pharmaceuticals, Inc.

[57] ABSTRACT

The present invention provides a human phospholemman homolog protein (HPLMH) and polynucleotides which identify and encode HPLMH. The invention also provides genetically engineered expression vectors and host cells comprising the nucleic acid sequences encoding HPLMH. The invention also provides for the use of HPLMH, and antibodies, or agonists or antagonists specifically binding HPLMH, in the prevention and treatment of diseases associated with expression of HPLMH. Additionally the invention provides for the use of antisense molecules to polynucleotides encoding HPLMH for the treatment of diseases associated with the expression of HPLMH. The invention also provides diagnostic assays which utilize the polynucleotide, or fragments or the complement thereof, and antibodies specifically binding HPLMH.

8 Claims, 4 Drawing Sheets

```
                9                18                27                36                45                54
5' TGN GTC CAG CTC TGG GCC AGG GGG TCC AAA GTG CTC AGC CCC CGG GGC ACA GCA 63                72                81                90                99               108
    GGA CGT TTG GGG GCC TTC TTT CAG CAG GGG ACA GCC CGA TTG GGG ACA ATG GCG
                                                                        M   A 117               126               135               144               153               162
    TCT CTT GGC CAC ATC TTG GTT TTC TGT GTG GGT CTC CTC ACC ATG GCC AAG GCA
     S   L   G   H   I   L   V   F   C   V   G   L   L   T   M   A   K   A 171               180               189               198               207               216
    GAA AGT CCA AAG GAA CAC GAC CCG TTC ACT TAC GAC TAC CAG TCC CTG CAG ATC
     E   S   P   K   E   H   D   P   F   T   Y   D   Y   Q   S   L   Q   I 225               234               243               252               261               270
    GGA GGC CTC GTC ATC GCC GGG ATC CTC TTC ATC CTG GGC ATC CTC ATC GTG CTG
     G   G   L   V   I   A   G   I   L   F   I   L   G   I   L   I   V   L 279               288               297               306               315               324
    AGC AGA AGA TGC CGG TGC AAG TTC AAC CAG CAG CAG AGG ACT GGG GAA CCC GAT
     S   R   R   C   R   C   K   F   N   Q   Q   Q   R   T   G   E   P   D 333               342               351               360               369               378
    GAA GAG GAG GGA ACT TTC CGC AGC TCC ATC CGC CGT CTG TCC ACC CGC AGG CGG
     E   E   E   G   T   F   R   S   S   I   R   R   L   S   T   R   R   R 387               396               405               414               423               432
    TAG AAA CAC CTG GAG CGA TGG AAT CCG GCC AGG ACT KCC CTG GCA CCT GAC ATC
     *

441               450               459               468               477               486
    TCC ACG GTC CAC CTG CGC GKC CAC CKW YCC CTT CGN CGG CCC TTT CCC AGC CCT 495               504               513               522               531               540
    GCC CCC GCA GAT TCC CCC TTG CCG CAA GGG TTT CCA TAA AGT GGT TTC TTT TGA

549
    AAA AAA GAG GGA TT 3'
```

FIGURE 1

```
1   M A S L G - H I L V F C V G L L T M A K A E S P K E H D P F   HPLMH
1   M A P L H - H I L V L C V G F L T T A T A E A P Q E H D P F   GI 108084
1   M Q K V T L G L L V F L A G F P V L D A N D L E D K N S P F   GI 1085026
1   M E G I T C A F L L V L A G L P V L E A N G P V D K G S P F   GI 951423
1   M V A V Q - - - - - - - - - - - - - - - - - G T E N P F       GI 51112

30  T Y D Y Q S L Q I G G L V I A G I L F I L G I L I V L S R R   HPLMH
30  T Y D Y Q S L R I G G L I I A G I L F I L G I L I V L S R R   GI 108084
31  Y Y D W H S L Q V G G L I C A G V L C A M G I I I V M S A K   GI 1085026
31  Y Y D W E S L Q L G G M I F G G L L C I A G I A M A L S G K   GI 951423
12  E Y D Y E T V R K G G L I F A G L A F V V G L L I L S K R     GI 51112

60  C R C K F N Q Q R T G E P D E E E G T F R S S I R R L S T     HPLMH
60  C R C K F N Q Q R T G E P D E E E G T F R S S I R R L S T     GI 108084
61  C K C K F G Q K - - S G H H P G E T P P L I T P - - - - G S   GI 1085026
61  C K C R R N H T - - P S S L P E K V T P L I T P - - - - G S   GI 951423
42  F R C G G G K K H R Q V N E D E L                             GI 51112

90  R R R                                                        HPLMH
90  R R R                                                        GI 108084
85  A Q S                                                        GI 1085026
85  A S T                                                        GI 951423
58                                                               GI 51112
```

FIGURE 2

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 92 amino acids
      (B) TYPE: amino acid
      (C) STRANDEDNESS: single
      (D) TOPOLOGY: linear (ii) MOLECULE TYPE: peptide

```
      (vii) IMMEDIATE SOURCE:
            (A) LIBRARY: PROSNOT05
            (B) CLONE: 786812

(xi) SEQUENCE DESCRIPTION: SEQ ID NO:1:

Met Ala Ser Leu Gly His Ile Leu Val Phe Cys Val Gly Leu Thr
 1               5                  10                  15

Met Ala Lys Ala Glu Ser Pro Lys Glu His Asp Pro Phe Thr Tyr Asp
            20                  25                  30

Tyr Gln Ser Leu Gln Ile Gly Gly Leu Val Ile Ala Gly Ile Leu Phe
            35                  40                  45

Ile Leu Gly Ile Leu Ile Val Leu Ser Arg Arg Cys Arg Cys Lys Phe
        50                  55                  60

Asn Gln Gln Gln Arg Thr Gly Glu Pro Asp Glu Glu Glu Gly Thr Phe
 65                 70                  75                  80

Arg Ser Ser Ile Arg Arg Leu Ser Thr Arg Arg Arg
                85                  90

(2) INFORMATION FOR SEQ ID NO:2:

(i) SEQUENCE CHARACTERISTICS:
            (A) LENGTH: 554 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (A) LIBRARY: PROSNOT05
            (B) CLONE: 786812

(xi) SEQUENCE DESCRIPTION: SEQ ID NO:2:

TGNGTCCAGC TCTGGGCCAG GGGGTCCAAA GTGCTCAGCC CCGGGGCAC AGCAGGACGT      60

TTGGGGGCCT TCTTTCAGCA GGGGACAGCC CGATTGGGGA CAATGGCGTC TCTTGGCCAC    120

ATCTTGGTTT TCTGTGTGGG TCTCCTCACC ATGGCCAAGG CAGAAAGTCC AAAGGAACAC    180

GACCCGTTCA CTTACGACTA CCAGTCCCTG CAGATCGGAG GCCTCGTCAT CGCCGGGATC    240

CTCTTCATCC TGGGCATCCT CATCGTGCTG AGCAGAAGAT GCCGGTGCAA GTTCAACCAG    300

CAGCAGAGGA CTGGGGAACC CGATGAAGAG GAGGGAACTT TCCGCAGCTC CATCCGCCGT    360

CTGTCCACCC GCAGGCGGTA GAAACACCTG GAGCGATGGA ATCCGGCCAG GACTKCCCTG    420

GCACCTGACA CTCCACGGT CCACCTGCGC GKCCACCKWY CCCTTCGNCG GCCCTTTCCC     480

AGCCCTGCCC CCGCAGATTC CCCCTTGCCG CAAGGGTTTC CATAAAGTGG TTTCTTTTGA    540

AAAAAAGAGG GATT                                                    554

(2) INFORMATION FOR SEQ ID NO:3:

(i) SEQUENCE CHARACTERISTICS:
            (A) LENGTH: 92 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (A) LIBRARY: GenBank
            (B) CLONE: 108084

(xi) SEQUENCE DESCRIPTION: SEQ ID NO:3:

Met Ala Pro Leu His His Ile Leu Val Leu Cys Val Gly Phe Leu Thr
 1               5                  10                  15
```

```
Thr Ala Thr Ala Glu Ala Pro Gln Glu His Asp Pro Phe Thr Tyr Asp
            20                  25                  30

Tyr Gln Ser Leu Arg Ile Gly Gly Leu Ile Ile Ala Gly Ile Leu Phe
            35                  40                  45

Ile Leu Gly Ile Leu Ile Val Leu Ser Arg Arg Cys Arg Cys Lys Phe
50                  55                  60

Asn Gln Gln Gln Arg Thr Gly Glu Pro Asp Glu Glu Glu Gly Thr Phe
65                  70                  75                  80

Arg Ser Ser Ile Arg Arg Leu Ser Thr Arg Arg Arg
                85                  90

(2) INFORMATION FOR SEQ ID NO:4:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1085026

(xi) SEQUENCE DESCRIPTION: SEQ ID NO:4:

Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Asp Trp His Ser Leu Gln Val Gly Gly Leu Ile Cys Ala Gly Val Leu
            35                  40                  45

Cys Ala Met Gly Ile Ile Ile Val Met Ser Ala Lys Cys Lys Cys Lys
50                  55                  60

Phe Gly Gln Lys Ser Gly His His Pro Gly Glu Thr Pro Pro Leu Ile
65                  70                  75                  80

Thr Pro Gly Ser Ala Gln Ser
                85

(2) INFORMATION FOR SEQ ID NO:5:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 951423

(xi) SEQUENCE DESCRIPTION: SEQ ID NO:5:

Met Glu Gly Ile Thr Cys Ala Phe Leu Leu Val Leu Ala Gly Leu Pro
1               5                   10                  15

Val Leu Glu Ala Asn Gly Pro Val Asp Lys Gly Ser Pro Phe Tyr Tyr
            20                  25                  30

Asp Trp Glu Ser Leu Gln Leu Gly Gly Met Ile Phe Gly Gly Leu Leu
            35                  40                  45

Cys Ile Ala Gly Ile Ala Met Ala Leu Ser Gly Lys Cys Lys Cys Arg
50                  55                  60
```

```
Arg Asn His Thr Pro Ser Ser Leu Pro Glu Lys Val Thr Pro Leu Ile
65                  70                  75                  80

Thr Pro Gly Ser Ala Ser Thr
                85

(2) INFORMATION FOR SEQ ID NO:6:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 51112

(xi) SEQUENCE DESCRIPTION: SEQ ID NO:6:

Met Val Ala Val Gln Gly Thr Glu Asn Pro Phe Glu Tyr Asp Tyr Glu
1                5                  10                  15

Thr Val Arg Lys Gly Gly Leu Ile Phe Ala Gly Leu Ala Phe Val Val
                20                  25                  30

Gly Leu Leu Ile Ile Leu Ser Lys Arg Phe Arg Cys Gly Gly Gly Lys
                35                  40                  45

Lys His Arg Gln Val Asn Glu Asp Glu Leu
        50                  55
```

HUMAN PHOSPHOLEMMAN HOMOLOG

FIELD OF THE INVENTION

This invention relates to nucleic acid and amino acid sequences of a novel human phospholemman homolog protein and to the use of these sequences in the diagnosis, prevention, and treatment of diseases of the central nervous system, cardiovascular system, prostate, and disorders related to smooth muscle function.

BACKGROUND OF THE INVENTION

Phospholemman (PLM) is the major plasmalemmal substrate for cAMP-dependent protein kinase (cAMPK) and protein kinase C (PKC). Canine and murine PLM are expressed at high levels in heart, skeletal muscle, and liver, and at low levels in breast, brain, lung, stomach, kidney, and colon (Palmer C. et al. (1991) J Biol Chem 266:11126–11130; Moorman J. R. et al. (1992) J Biol Chem 267:14551–14554). PLM is a membrane protein which consists of 72 amino acids and has a calculated molecular weight of 8409. The native protein has an apparent molecular weight of 15 kDa as determined following polyacrylamide gel electrophoresis. A distinguishing feature of PLM is its highly basic nature, with a calculated isoelectric point of 9.7 (Palmer C. et al., supra). PLM consists of an acidic extracellular amino-terminal domain, a single uncharged transmembrane domain, and an extremely basic cytoplasmic carboxy-terminal domain. The cytoplasmic domain contains consensus cAMPK and PKC phosphorylation sites. The phosphorylation of PLM by PKC and cAMPK is regulated by insulin and adrenaline, respectively (Walaas S. et al. (1994) Biochem J 304:635–640). PLM phosphorylation in cardiac muscle occurs after activation of either α- or β adrenergic receptors, and correlates with an increase in contractility (Lindemann JP (1986) J Biol Chem 261:4860–4867).

Expression of PLM in Xenopus oocytes injected with PLM mRNA coincides with the appearance of voltage-activated chloride currents (Moorman et al., supra). Immunoaffinity-purified recombinant PLM added to planar phospholipid bilayers produces unitary anion currents (Moorman J. R. et al. (1995) Nature 377:737–740). The high selectivity of the PLM channel for the sulfonic amino acid taurine suggests that PLM channels link signal transduction cascades to cell volume regulation. PLM is the smallest membrane protein known to form an ion channel (Moorman et al. (1995), supra).

Mat-8, an 8-kDa transmembrane protein related to PLM, is expressed in murine breast tumor lines transformed by Neu or Ras oncoproteins. Morrison B. W. et al. ((1994) Oncogene 9:3417–3426) proposed that Mat-8 is a marker of the cell type preferentially transformed by neu or v-Ha-ras oncogenes. A human Mat-8 homolog is expressed both in primary breast tumors and in breast tumor cell lines. Murine Mat-8 is also expressed in uterus, stomach, colon, and at low levels in virgin breast, ovary, lung, small intestine and thymus. In contrast to PLM, Mat-8 is not expressed in liver, heart or skeletal muscle, which suggests distinct cellular functions for the two molecules (Morrison B. W. et al. (1995) J Biol Chem 270:2176–2182).

The extracellular and transmembrane domains of Mat-8 are homologous to those of PLM. However, the cytoplasmic domain of Mat-8 is unrelated to PLM and contains no consensus phosphorylation sites for PKC or cAMPK. Expression of Mat-8 in Xenopus oocytes induces voltage-activated Cl⁻ currents similar to those induced by expression of PLM (Morrison et al. (1995), supra), but direct ion channel formation by Mat-8 has not been reported. The ability of Mat-8 protein to induce Cl⁻ channel activity, together with its tissue distribution (see above), suggests that this protein may be involved in the regulation of transepithelial transport in tissues containing absorptive or secretory epithelia.

Additional proteins similar in structure to PLM and Mat-8 have been found to induce ion channel activity when expressed in Xenopus oocytes. Channel-inducing factor (CHIF), found in colon and kidney, consists of a single transmembrane domain and exhibits 50% sequence similarity to PLM (Attali B. et al. (1995) Proc Natl Acad Sci USA 92:6092–6096). Xenopus oocytes injected with CHIF mRNA exhibit K⁺ specific channel activity. Slow-activating voltage dependent potassium ion channel (IsK; Takumi T. et al. (1988) Science 242:1042–1045) is a single transmembrane domain glycoprotein present in epithelial cells, heart, uterus and lymphocytes (Attali B. et al. (1993) Nature 365:850–852). IsK induces both K⁺ and Cl⁻ currents when expressed in Xenopus oocytes and HEK293 cells. The accumulated evidence suggests that CHIF and IsK act as regulatory subunits of pre-existing channel complexes rather than as channels per se (Attali B. et al. (1995), supra; Ben-Efraim I. et al. (1996) J Biol Chem 271:8768–8771).

The sodium, potassium ATPase (Na,K-ATPase) γ-subunit, formerly known as the Na,K-ATPase proteolipid, is a small membrane protein that co-purifies with the α- and β-subunits of Na,K-ATPase (Mercer R. W. et al. (1993) J Cell Biol 121:579–586). The γ-subunit contains 58 amino acids with a single transmembrane domain. This transmembrane domain is structurally related to the transmembrane domains of other PLM-like proteins. The γ-subunit may act as a regulator of the ATP-dependent ion channel activity of Na,K-ATPase.

The polynucleotide sequence and polypeptides encoding a human phospholemman homolog protein associated with neurotransmitter release, transepithelial transport, membrane potential stabilization, signal transduction, and cell volume regulation would satisfy a need in the art by providing a new means for the diagnosis, prevention, or treatment of diseases of the central nervous system such as Alzheimer's disease, Parkinson's disease, Huntington's disease, Creutzfeld-Jacob disease, amyotrophic lateral sclerosis, and hydrocephalus; diseases of the cardiovascular system such as angina, cardiac hypertrophy, congestive heart failure, vasoconstriction, and hypertension, prostate hypertrophy, and disorders related to smooth muscle function such as bladder and sphincter dysfunction, bronchial constriction, and asthma.

SUMMARY OF THE INVENTION

The present invention features a novel human phospholemman homolog protein hereinafter designated HPLMH and characterized by having homology to canine PLM, MAT-8, CHIF, and (Na,K-ATPase) γ-subunit and acting as an ion channel with preference for chloride ions and/or taurine.

Accordingly, the invention features a substantially purified human phospholemman homolog protein having ion channel activity, an amino-terminal signal sequence, and a single transmembrane domain and having the amino acid sequence of SEQ ID NO:1.

One aspect of the invention features isolated and substantially purified polynucleotides that encode HPLMH. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HPLMH. The present invention also features antibodies which bind specifically to HPLMH and pharmaceutical compositions comprising substantially purified HPLMH. The invention also features agonists and antagonists of HPLMH and the use thereof

BRIEF DESCRIPTION OF THE FIGURES

FIG. 1 shows the amino acid sequence (SEQ ID NO:1) and nucleic acid sequence (SEQ ID NO:2) of HPLMH. The alignment was produced using MacDNAsis PRO™ software (Hitachi Software Engineering Co., Ltd, San Bruno, Calif.).

FIG. 2 shows the amino acid sequence alignments among HPLMH (SEQ ID NO:1), canine PLM (SEQ ID NO:3, GI 108084; Palmer et al., supra), human MAT-8 (SEQ ID NO:4, GI 1085026; Morrison et al., supra), rat CHIF (SEQ ID NO:5, GI 951423; Attali B. et al. (1995), supra), and mouse Na,K-ATPase γ-subunit (SEQ ID NO:6, GI 51112; Mercer R. W. et al., supra). The alignment was produced using the multisequence alignment program of DNASTAR™ software (DNASTAR Inc., Madison Wis.).

DESCRIPTION OF THE INVENTION

Figure 3:
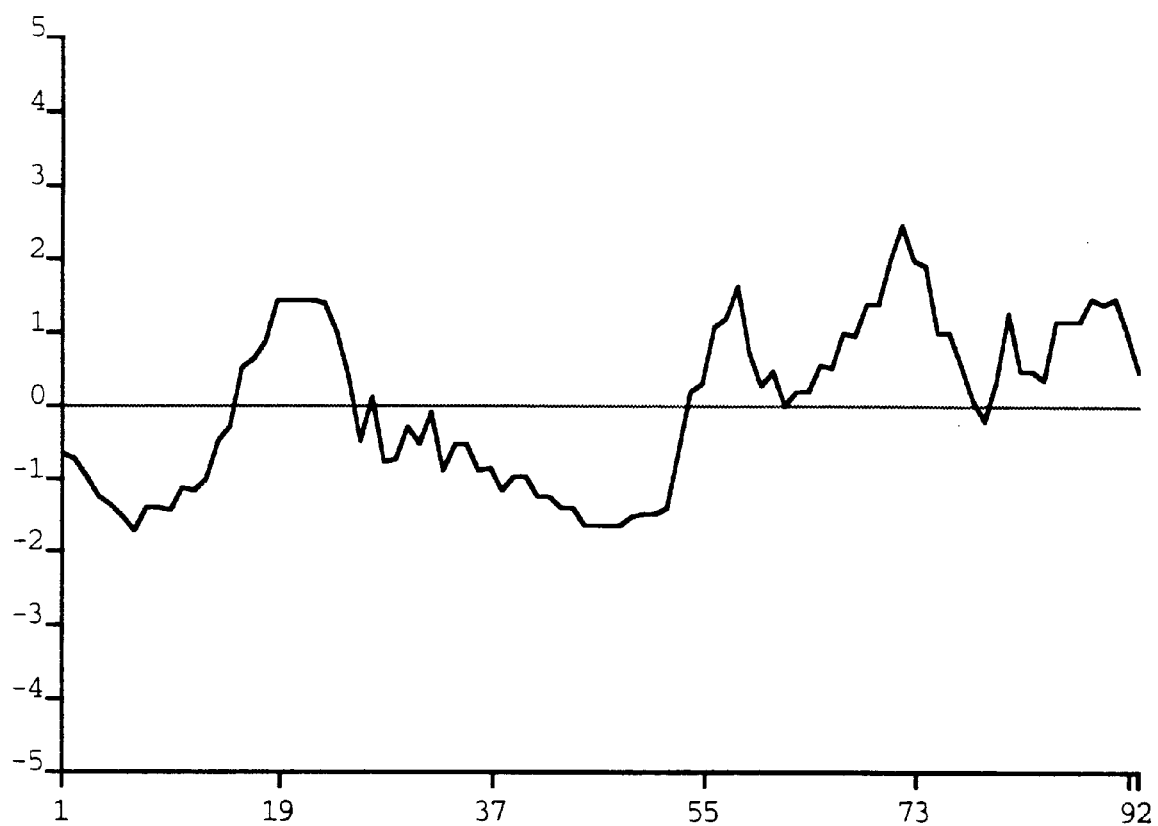
FIG. 3 shows the hydrophobicity plot (generated using MacDNAsis PRO software) for HPLMH (SEQ ID NO:1); the positive X axis reflects amino acid position, and the negative Y axis, hydrophobicity.

Before the present protein, nucleotide sequence, and methods are described, it is understood that this invention is not limited to the particular methodology, protocols, cell lines, vectors, and reagents described as these may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen et al. (1993) *Anticancer Drug Des* 8:53–63).

HPLMH, as used herein, refers to the amino acid sequences of substantially purified HPLMH obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GCG Fragment Assembly™ system (GCG, Madison Wis.), or which has been both extended and assembled.

A "variant" of HPLMH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HPLMH, or any oligopeptide thereof, to induce a specific immune response in appropriate animals or cells and to bind with specific antibodies.

The term "agonist", as used herein, refers to a molecule which, when bound to HPLMH, causes a change in HPLMH which modulates the activity of HPLMH. Agonists may include proteins, nucleic acids, carbohydrates, or any other molecules which bind to HPLMH.

The terms "antagonist" or "inhibitor", as used herein, refer to a molecule which, when bound to HPLMH, blocks the binding of an agonist to HPLMH, which prevents the agonist-induced change in the biological activity of HPLMH. Antagonists may include proteins, nucleic acids, carbohydrates, or any other molecules which bind to HPLMH.

The term "modulate", as used herein, refers to a change or an alteration in the biological activity of HPLMH. Modulation may be an increase or a decrease in biological activity, a change in binding characteristics, or any other change in the biological properties of HPLMH.

The term "mimetic", as used herein, refers to a molecule, the structure of which is developed from knowledge of the structure of human phospholemman homolog protein or portions thereof and, as such, is able to effect some or all of the actions of human phospholemman homolog protein.

The term "derivative", as used herein, refers to the chemical modification of a nucleic acid encoding HPLMH or the encoded HPLMH. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach et al. (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" bonds to the complementary sequence "T-C-A". Complementarity between two single-stranded molecules may be "partial", in which only some of the nucleic acids bind, or it may be complete when total complementarity exists between the single-stranded molecules. The degree of complementarity between nucleic acid strands has significant effects on the efficiency and strength of hybridization between nucleic acid strands. This is of particular importance in amplification reactions, which depend upon binding between the nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to RNA sequences which are complementary to a specific RNA sequence (e.g., mRNA). Antisense RNA may be produced by any method, including synthesis by ligating the gene(s) of interest in a reverse orientation to a viral promoter which permits the synthesis of a complementary-coding strand. Once introduced into a cell, this transcribed strand combines with natural mRNA produced by the cell to form duplexes. These duplexes then block the further translation of the mRNA. In this manner, mutant phenotypes may be generated. The term "antisense strand" is used in reference to a nucleic acid strand that is complementary to the "sense" strand. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1 encompasses the full-length human HPLMH and fragments thereof.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HPLMH or fragments thereof may comprise a cell, chromosomes isolated from a cell (e.g., a spread of metaphase chromosomes), genomic DNA (in solution or bound to a solid support such as for Southern blot analysis), RNA (in solution or bound to a solution or bound to a solid support such as for northern blot analysis), cDNA (in solution or bound to a solid support), an extract from cells or a tissue containing one or more proteins, and the like.

The term "correlates with expression of a polynucleotide", as used herein, indicates that the detection of the presence of ribonucleic acid that is complementary to SEQ ID NO:2 by northern analysis hybridization assays is indicative of the presence of mRNA encoding HPLMH in a sample and thereby correlates with expression of the transcript from the gene encoding the protein.

"Alterations" in the polynucleotide of SEQ ID NO:2, as used herein, comprise any alteration in the sequence of polynucleotides encoding HPLMH including deletions, insertions, and point mutations that may be detected using hybridization assays. Included within this definition is the detection of alterations to the genomic DNA sequence which encodes HPLMH (e.g., by alterations in the pattern of restriction enzyme fragments capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the gene encoding HPLMH (e.g., using FISH to metaphase chromosomes spreads).

The terms "transformed" and "transformation", as used herein, refer to any known method for the insertion of foreign DNA or RNA sequences into host prokaryotic or eukaryotic cells. It may occur under natural or artificial conditions using various methods well known in the art. Such transformed cells include cells in which the inserted DNA is capable of replication either as an autonomously replicating plasmid or as part of the host chromosome in the host cell. They also include cells which transiently express the inserted DNA or RNA for limited periods of time. The transformation method depends on the host cell being transformed. Methods of transformation are well known in the art and include, but are not limited to, viral infection, electroporation, lipofection, and calcium phosphate mediated direct uptake.

As used herein, the term "antibody" refers to intact molecules as well as fragments thereof, such as Fa, F(ab')$_2$, and Fv, which are capable of binding the epitopic determinant. Antibodies that bind HPLMH polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of the human phospholemman homolog protein, HPLMH, the polynucleotides encoding HPLMH, and the use of these compositions for the diagnosis, prevention or treatment of diseases of the central nervous system, cardiovascular system, prostate, and disorders related to smooth muscle function.

Nucleic acids encoding the HPLMH of the present invention were first identified in cDNA in Incyte Clone 786812 (SEQ ID NO:2) from a normal human prostate cDNA library (PROSNOT05) through a computer-generated search for amino acid sequence alignments.

In one embodiment, the invention encompasses human phospholemman homolog, a protein comprising the amino acid sequence of SEQ ID NO:1, as shown in FIG. 1. HPLMH is 92 amino acids in length. HPLMH has chemical and structural homology with PLM (SEQ ID NO:3; GI 108084), MAT-8 (SEQ ID NO:4; GI 1085026), CHIF (SEQ ID NO:5; GI 951423), and Na,K-ATPase γ-subunit (SEQ ID NO:6; GI 51112). PLM, Mat-8, CHIF, and Na,K-ATPase γ-subunit have, respectively, 90%, 33%, 22%, and 25% sequence identity to HPLMH. The amino acid identity between HPLMH (SEQ ID NO:1) and PLM (SEQ ID NO:3) increases to 94% when the signal peptide sequence is excluded from the comparison; the remaining 4 differences between HPLMH and PLM are conservative amino acid replacements.

Figure 4:
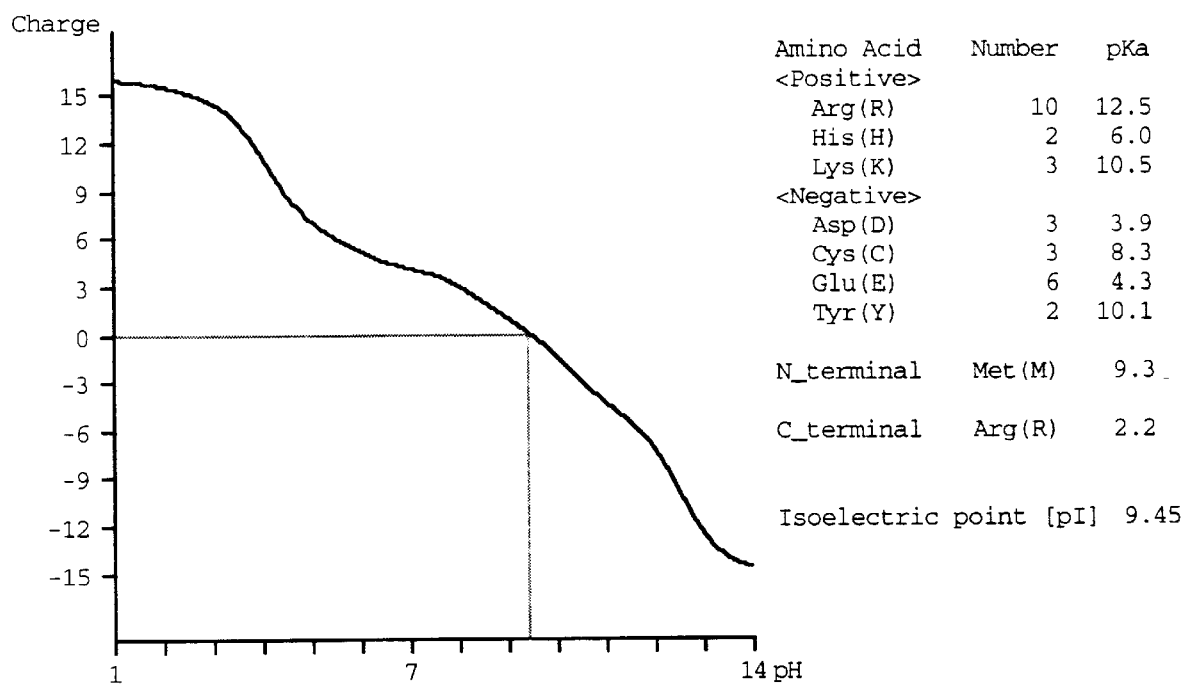
FIG. 4 shows the plot (generated using MacDNAsis PRO software) used to calculate the isoelectric point (pI) of HPLMH.

From the amino acid sequence alignments (FIG. 2) and the hydrophobicity plot for HPLMH (FIG. 3), the HPLMH signal peptide is predicted to extend from residue 1 to residue 20. A single transmembrane domain is predicted to extend from residue 38 to residue 57 of HPLMH, using the numbering of SEQ ID NO:1, and terminates in a positively-charged membrane stop transfer sequence (RRCRCK) at residue 58 to residue 63. Both HPLMH and PLM are highly basic proteins with predicted isoelectric points of 9.45 (FIG. 4) and 9.7 (Palmer C. et al., supra), respectively, which suggests that they have a similar structure.

The invention also encompasses HPLMH variants. A preferred HPLMH variant is one having at least 80%, and more preferably 90%, amino acid sequence similarity to the HPLMH amino acid sequence (SEQ ID NO:1). A most preferred HPLMH variant is one having at least 95% amino acid sequence similarity to SEQ ID NO:1.

The invention also encompasses polynucleotides which encode HPLMH. Accordingly, any nucleic acid sequence which encodes the amino acid sequence of HPLMH can be used to generate recombinant molecules which express HPLMH. In a particular embodiment, the invention encompasses the polynucleotide comprising the nucleic acid of SEQ ID NO:2 as shown in FIG. 1.

It will be appreciated by those skilled in the art that as a result of the degeneracy of the genetic code, a multitude of nucleotide sequences encoding HPLMH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HPLMH, and all such variations are to be considered as being specifically disclosed.

Although nucleotide sequences which encode HPLMH and its variants are preferably capable of hybridizing to the nucleotide sequence of the naturally occurring HPLMH under appropriately selected conditions of stringency, it may be advantageous to produce nucleotide sequences encoding HPLMH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPLMH and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HPLMH and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HPLMH or any portion thereof.

Also encompassed by the invention are polynucleotide sequences that are capable of hybridizing to the claimed nucleotide sequences, and in particular, those shown in SEQ ID NO:2 under various conditions of stringency. Hybridization conditions are based on the melting temperature (Tm) of the nucleic acid binding complex or probe, as taught in Berger and Kimmel 1987, *Guide to Molecular Cloning Techniques, Methods in Enzymology*, Vol 152, Academic Press, San Diego, Calif.), and may be used at a defined stringency.

Altered nucleic acid sequences encoding HPLMH which are encompassed by the invention include deletions, insertions, or substitutions of different nucleotides resulting in a polynucleotide that encodes the same or a functionally equivalent HPLMH. The encoded protein may also contain deletions, insertions, or substitutions of amino acid residues which produce a silent change and result in a functionally equivalent HPLMH. Deliberate amino acid substitutions may be made on the basis of similarity in polarity, charge, solubility, hydrophobicity, hydrophilicity, and/or the amphipathic nature of the residues as long as the biological activity of HPLMH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are encoded alleles of the gene encoding HPLMH. As used herein, an "allele" or "allelic sequence" is an alternative form of the gene for HPLMH which may result from a mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The polynucleotide sequence encoding HPLMH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar G. et al. (1993); PCR Methods Applic 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al. (1988) Nucleic Acids Res 16:8186). The primers may be designed using OLIGO® 4.06 Primer Analysis Software (1992; National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al. (1991) PCR Methods Applic 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker et al. (1991; Nucleic Acids Res 19:3055–3060). Additionally, one may use PCR, nested primers, and PromoterFinder™ libraries to walk in genomic DNA (Clontech, Palo Alto, Calif.). This process avoids the need to screen libraries and may be useful in finding intron/exon junctions.

When screening for full-length cDNAs, it is preferable to use libraries that have been size-selected to include larger cDNAs. Also, random-primed libraries are preferable in that they will contain more sequences which contain the 5' regions of the mRNA. Use of a randomly primed library may be especially preferable for situations in which an oligo d(T) library does not yield a full-length cDNA. Genomic libraries may be useful for extension of sequence into the 5' and 3' regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g., Genotyper™ and Sequence Navigator™ from Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HPLMH, or fusion proteins or functional equivalents thereof, may be used in recombinant DNA molecules to direct expression of HPLMH in appropriate host cells. Due to the inherent degeneracy of the genetic code, other DNA sequences which encode substantially the same or a functionally equivalent amino acid sequence may be produced and these sequences may be used to clone and express HPLMH.

As will be understood by those of skill in the art, it may be advantageous to produce HPLMH-encoding nucleotide sequences possessing non-naturally occurring codons. For example, codons preferred by a particular prokaryotic or eukaryotic host can be selected to increase the rate of HPLMH expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HPLMH coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HPLMH may be ligated to a heterologous sequence to encode a fusion protein. For example, to screen peptide libraries for inhibitors of HPLMH activity, it may be useful to encode a chimeric HPLMH protein that can be recognized by a commercially available antibody. A fusion protein may also be engineered to contain a cleavage site located between a HPLMH encoding sequence and the heterologous protein sequence, so that the HPLMH may be cleaved and purified away from the heterologous moiety.

In another embodiment, the coding sequence of HPLMH may be synthesized, in whole or in part, using chemical methods well known in the art (see Caruthers et al. (1980) Nucleic Acids Res Symp Ser 215–223, Horn et al. (1980) Nucleic Acids Res Symp Ser 225–232, etc.). Alternatively, the protein itself may be produced using chemical methods to synthesize the HPLMH amino acid sequence, or a portion thereof. For example, peptide synthesis can be performed using various solid-phase techniques (Roberge et al. (1995) Science 269:202–204) and automated synthesis may be achieved, for example, using the ABI 431 A Peptide Synthesizer (Perkin Elmer).

The newly synthesized peptide may be substantially purified by preparative high performance liquid chromatography (e.g., Creighton (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HPLMH, or any part thereof, may be altered during direct synthesis and/or combined using chemical methods with sequences from other proteins, or any part thereof, to produce a variant polypeptide.

In order to express a biologically active HPLMH, the nucleotide sequence encoding HPLMH or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HPLMH coding sequence and appropriate transcriptional and translational control elements. These methods include in vitro recombinant DNA techniques, synthetic techniques, and in vivo recombination or genetic recombination. Such techniques are described in Sambrook et al. (1989) *Molecular Cloning, A Laboratory Manual*, Cold Spring Harbor Press, Plainview, N.Y., and Ausubel et al. (1989) *Current Protocols in Molecular Biology*, John Wiley & Sons, New York, N.Y.

A variety of expression vector/host systems may be utilized to contain and express a HPLMH coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" are those non-translated regions of the vector, enhancers, promoters, 5' and 3' untranslated regions, which interact with host cellular proteins to carry out transcription and translation and they may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1 (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of HPLMH, vectors based on SV40 or EBV may be used with an appropriate selectable marker.

In bacterial systems, a number of expression vectors may be selected depending upon the use intended for HPLMH. For example, when large quantities of HPLMH are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the HPLMH coding sequence may be ligated into the vector in frame with sequences for the amino-terminal Met and the subsequent 7 residues of β-galactosidase so that a hybrid protein is produced; pIN vectors (Van Heeke and Schuster (1989) *J Biol Chem* 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods in Enzymol* 153:516–544.

In cases where plant expression vectors are used, the expression of a sequence encoding HPLMH may be driven by any of a number of promoters. For example, viral promoters such as the 35S and 19S promoters of CaMV may be used alone or in combination with the omega leader sequence from TMV (Takamatsu et al. (1987) EMBO J 6:307–311; Brisson et al. (1984) Nature 310:511–514). Alternatively, plant promoters such as the small subunit of RUBISCO; or heat shock promoters may be used (Coruzzi et al. (1984) EMBO J 3:1671–1680; Broglie et al. (1984) Science 224:838–843; Winter et al. (1991) Results Probl Cell Differ 17:85–105). These constructs can be introduced into plant cells by direct DNA transformation or pathogen-mediated transfection. Such techniques are described in a number of generally available reviews (see, for example, Hobbs, S or Murry, LE in McGraw Hill *Yearbook of Science and Technology* (1992) McGraw Hill, New York, NY; pp. 191–196 or Weissbach and Weissbach (1988) *Methods for Plant Molecular Biology*, Academic Press, New York, N.Y.; pp. 421–463).

An insect system may also be used to express HPLMH. For example, in one such system, *Autographa californica* nuclear polyhedrosis virus (*Ac*NPV) is used as a vector to express foreign genes in *Spodoptera frugiperda* cells or in *Trichoplusia larvae*. The HPLMH coding sequence may be cloned into a non-essential region of the virus, such as the polyhedrin gene, and placed under control of the polyhedrin promoter. Successful insertion of HPLMH will render the polyhedrin gene inactive and produce recombinant virus lacking coat protein. The recombinant viruses may then be used to infect, for example, *S. frugiperda* cells or *Trichoplusia larvae* in which HPLMH may be expressed (Smith et al. (1983) J Virol 46:584; Engelhard et al. (1994) Proc Nat Acad Sci 91:3224–3227).

In mammalian host cells, a number of viral-based expression systems may be utilized. In cases where an adenovirus is used as an expression vector, a HPLMH coding sequence may be ligated into an adenovirus transcription/translation complex consisting of the late promoter and tripartite leader sequence. Insertion in a non-essential E1 or E3 region of the viral genome may be used to obtain a viable virus which is capable of expressing HPLMH in infected host cells (Logan and Shenk (1984) Proc Natl Acad Sci 81:3655–3659). In addition, transcription enhancers, such as the Rous sarcoma virus (RSV) enhancer, may be used to increase expression in mammalian host cells.

Specific initiation signals may also be used to achieve more efficient translation of a HPLMH sequence. Such signals include the ATG initiation codon and adjacent sequences.

In cases where sequences encoding HPLMU, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf D. et al. (1994) Results Probl Cell Differ 20:125–162; Bittner et al. (1987) *Methods in Enzymol* 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, WI38, which have specific cellular machinery and characteristic mechanisms for such post-translational activities, may be chosen to ensure the correct modification and processing of the introduced foreign protein.

For long-term, high-yield production of recombinant proteins, stable expression is preferred. For example, cell lines which stably express HPLMH may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase and adenine phosphoribosyltransferase genes which can be employed in tk⁻ or aprt⁻ cells, respectively (Wigler M. et al. (1977) Cell 11:223–232 and Lowy et al. (1980) Cell 22:817–823). Also, antimetabolite, antibiotic, or herbicide resistance may be used as the basis for selection. For example, dhfr, which confers resistance to methotrexate, npt, which confers resistance to the aminoglycosides neomycin and G-418, and als or pat, which confer resistance to chlorsulfuron and phosphinotricin acetyltransferase, may be used (Wigler M. et al. (1980) Proc Natl Acad Sci 77:3567–3570 and Colbere-Garapin et al. (1981) J Mol Biol 150:1–14). Additional selectable genes may be used, for example, trpB, which allows cells to utilize indole in place of tryptophan, or hisD, which allows cells to utilize histinol in place of histidine (Hartman et al. (1988) Proc Natl Acad Sci 85:8047–8051). Also, visible markers such as green fluorescent protein, anthocyanins, β glucuronidase, and its substrate, GUS, and luciferase and its substrate, luciferin, may be used not only to identify transformants, but also to quantify the amount of transient or stable protein expression attributable to a specific vector system (Rhodes C. et al. (1995) *Methods Mol Biol* 55:121–131).

Although the presence/absence of marker gene expression suggests that the gene of interest is also present, its presence and expression may be confirmed. For example, if the sequence encoding HPLMH is inserted within a marker gene sequence, recombinant cells containing sequences encoding HPLMH can be identified by the absence of marker gene function. Alternatively, a marker gene can be placed in tandem with a HPLMH sequence under the control of a single promoter. Expression of the marker gene in response to induction or selection usually indicates expression of the tandem HPLMH as well. Alternatively, host cells which contain the coding sequence for HPLMH and express HPLMH may be identified by a variety of procedures known to those of skill in the art. These procedures include, but are not limited to, DNA-DNA or DNA-RNA hybridizations, fluorescent activated cell sorting and protein bioassay or immunoassay techniques which include membrane, solution, or chip based technologies for the detection and/or quantification of the nucleic acid or protein.

The presence of the polynucleotide sequence encoding HPLMH can be detected by DNA-DNA or DNA-RNA hybridization or amplification using probes or portions or fragments of polynucleotides encoding HPLMH. Nucleic acid amplification based assays involve the use of oligonucleotides or oligomers based on the HPLMH-encoding sequence to detect transformants containing DNA or RNA encoding HPLMH. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HPLMH, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HPLMH is preferred, but a competitive binding assay may be employed. These and other assays are described, among other places, in Hampton et al. (1990, *Serological Methods, a Laboratory Manual*, APS Press, St Paul, Minn.) and Maddox et al. (1983) J Exp Med 158:1211).

A wide variety of labels and conjugation techniques are known by those skilled in the art and may be used in various nucleic acid and amino acid assays. Means for producing labeled hybridization or PCR probes for detecting sequences related to polynucleotides encoding HPLMH include oligolabeling, nick translation, end-labeling or PCR amplification using a labeled nucleotide. Alternatively, the sequence encoding HPLMH, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. These procedures may be conducted using a variety of commercially available kits (Pharmacia and Upjohn, Kalamazoo, Mich., Promega, Madison, Wis., and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HPLMH may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides which encode HPLMH may be designed to contain signal sequences which direct secretion of HPLMH through a prokaryotic or eukaryotic cell membrane. Other recombinant constructions may be used to join sequences encoding HPLMH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of a cleavable linker sequences such as Factor XA or enterokinase (Invitrogen, San Diego, Calif.) between the purification domain and HPLMH may be used to facilitate purification. One such expression vector which may be used provides for expression of a fusion protein containing a HPLMH and a nucleic acid encoding 6 histidine residues followed by thioredoxin and an enterokinase cleavage site. The histidine residues facilitate purification on IMIAC (immobilized metal ion affinity chromatography as described in Porath et al. (1992) *Protein Expression and Purification* 3:263–281) while the enterokinase cleavage site provides a means for purifying HPLMH from the fusion protein. A discussion of vectors which contain fusion proteins is provided in Kroll et al. (1993) DNA Cell Biol 12:441–453.

In addition to recombinant production, fragments of HPLMH may be produced by direct peptide synthesis using solid-phase techniques (cf Stewart et al. (1969) *Solid-Phase Peptide Synthesis*, WH Freeman Co., San Francisco, Calif.; Maryfield J. (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer). Various fragments of HPLMH may be chemically synthesized separately and combined using chemical methods to produce the full length molecule.

THERAPEUTICS

Chemical and structural homology exists among HPLMH protein, canine PLM (SEQ ID NO:3; GI 108084), human MAT-8 (SEQ ID NO:4; GI 1085026), rat CHIF (SEQ ID NO:5; GI 951423), and mouse Na,K-ATPase γ-subunit (SEQ ID NO:6; GI 51112) (FIG. 2). In addition, northern analysis demonstrates that HPLMH molecules are expressed in prostate, nervous system tissues, muscle, uterus, breast, and lung.

From the homology and expression information provided above, and the known associations and functions of PLM-like transmembrane proteins in heart and other tissues, it appears that HPLMH plays a role in modifying or regulating ion currents, including those associated with $Cl^-$ and $Ca^{2+}$ ions, and/or taurine influx and efflux. Therefore, in another embodiment of the invention, HPLMH or fragments thereof may be used for therapeutic purposes. Altered or mutated activity, or altered expression of HPLMH may be associated with diseases and conditions relating, but are not limited, to defective ion transport, defects in signal transmission, membrane potential generation, or fluid volume regulation. Accordingly, HPLMH or derivatives thereof, may be used to treat central nervous system diseases such as Alzheimer's disease, Parkinson's disease, Huntington's disease, Creutzfeld-Jacob disease, amyotrophic lateral sclerosis, and hydrocephalus, cardiovascular diseases such as angina, cardiac hypertrophy, congestive heart failure, vasoconstriction, and hypertension, prostate hypertrophy, and smooth muscle disorders such as bladder and sphincter dysfunction, bronchial constriction, and asthma.

In another embodiment, antagonists which block or modulate the effect of HPLMH may be used in those situations where such inhibition is therapeutically desirable. Such antagonists or inhibitors may be produced using methods which are generally known in the art, and include particularly the use of purified HPLMH to produce antibodies or to screen libraries of pharmaceutical agents for those which specifically bind HPLMH. For example, in one aspect, antibodies which are specific for HPLMH may be used directly as an antagonist, or indirectly as a targeting or delivery mechanism for bringing a pharmaceutical agent to cells or tissue which express HPLMH.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HPLMH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HPLMH have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HPLMH amino acids may be fused with those of another protein such as keyhole limpet hemocyanin and antibody produced against the chimeric molecule.

Monoclonal antibodies to HPLMH may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol Today 4:72; Cote et al. (1983) Proc Natl Acad Sci 80:2026–2030; Cole et al. (1985) *Monoclonal Antibodies and Cancer Therapy*, Alan R. Liss Inc., New York, NY, pp. 77–96).

In addition, techniques developed for the production of "chimeric antibodies", the splicing of mouse antibody genes to human antibody genes to obtain a molecule with appropriate antigen specificity and biological activity, can be used (Morrison et al. (1984) Proc Natl Acad Sci 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HPLMH-specific single chain antibodies. Antibodies with related specificity but of distinct idiotypic composition may be generated by chain shuffling from random combinatorial immnunoglobin libraries (Burton D. R. (1991) Proc Natl Acad Sci 88:11120–3).

Antibodies may also be produced by inducing in vivo production in the lymphocyte population or by screening recombinant immunoglobulin libraries or panels of highly specific binding reagents as disclosed in the literature (Orlandi et al. (1989) Proc Natl Acad Sci 86:3833–3837; Winter et al. (1991), Nature 349:293–299).

Antibody fragments which contain specific binding sites for HPLMH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPLMH and its specific antibody. A two-site, monoclonal-based immunoassay utilizing monoclonal antibodies reactive to two non-interfering epitopes on a specific HPLMH protein is preferred, but a competitive binding assay may also be employed (Maddox et al. (1983) J Exp Med 158:1211).

In another embodiment of the invention, the polynucleotides encoding HPLMH, or any fragment thereof or antisense sequences, may be used for therapeutic purposes. In one aspect, antisense to the polynucleotide encoding HPLMH may be used in situations in which it would be desirable to block the synthesis of HPLMH. In particular, cells may be transformed with antisense sequences to polynucleotides encoding HPLMH. Thus, antisense sequences may be used to achieve regulation of gene function. Such technology is now well known in the art, and sense or antisense oligomers or larger fragments, can be designed from various locations along the coding or control regions.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HPLMH. See, for example, the techniques described in Sambrook et al. (supra) and Ausubel et al. (supra).

Genes encoding HPLMH can be turned off by transforming a cell or tissue with expression vectors which express high levels of a polynucleotide or fragment thereof which encodes HPLMH. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HPLMH, i.e., the promoters, enhancers, and introns. Oligonucleotides derived from the transcription initiation site, e.g., between positions −10 and +10 from the 5' end of the transcript, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee et al., in Huber and Carr (1994) *Molecular and Immunologic Approaches*, Futura Publishing Co., Mt. Kisco, N.Y.). Antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HPLMH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPLMH. Such DNA sequences may be incorporated into a wide variety of vectors with suitable RNA polymerase promoters such as T7 or SP6. Alternatively, cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'-O-methyl-ribose within the phosphodiester backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Methods for introducing vectors into cells or tissues include those methods discussed above. These methods are equally suitable for use in in vivo, in vitro and ex vivo therapy. For ex vivo therapy, vectors may be introduced into stem cells taken from the patient and clonally propagated for autologous transplant back into that same patient. Delivery by transformation and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HPLMH, antibodies to HPLMH, mimetics, agonists, antagonists, or inhibitors of HPLMH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid paraffin or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt that can be formed with either an acid or base, depending on the nature of the therapeutic compound. Such acids include, but are not limited to, hydrochloric, sulfuric, acetic, lactic, tartaric, malic, and succinic; bases include, but are not limited to, sodium hydroxide and potassium hydroxide. Salts tend to be more soluble in aqueous or other protonic solvents than are the corresponding free acid or base forms. In other cases, the preferred preparation may be a lyophilized powder which may contain any or all of the following: 1 mM-50 mM histidine, 0.1%–2% sucrose, and 2%–7% mannitol, in a pH range of 4.5 to 5.5, that is/are combined with buffer prior to use.

After pharmaceutical compositions have been prepared, they can be placed in an appropriate container and labeled for treatment of an indicated condition. For administration of HPLMH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs or pigs. The animal model may also be used to determine the appropriate concentration range and route of administration. Such information can then be used to determine useful doses and routes for administration in humans.

A therapeutically effective dose refers to that amount of active ingredient, for example HPLMH or fragments thereof, antibodies to HPLMH or agonists, antagonists or inhibitors of HPLMH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject which requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which are specific for HPLMH may be used for the diagnosis of conditions or diseases characterized by expression of HPLMH, or in assays to monitor patients being treated with HPLMH, agonists, antagonists or inhibitors. The antibodies useful for diagnostic purposes may be prepared in the same manner as those described above for therapeutics. Diagnostic assays for HPLMH include methods which utilize the antibody and a label to detect HPLMH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring HPLMH, using either polyclonal or monoclonal antibodies specific for the respective protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HPLMH is preferred, but a competitive binding assay may be employed.

In order to provide a basis for diagnosing abnormal levels of HPLMH expression, normal or standard values for HPLMH expression are established. This may be accomplished by combining body fluids or cell extracts taken from normal mammalian subjects, preferably human, with antibody to HPLMH under conditions suitable for complex formation which are well known in the art. The amount of standard complex formation may be quantified by comparing various artificial membranes containing known quantities of HPLMH with both control and disease samples from biopsied tissues. Then, standard values obtained from normal samples may be compared with values obtained from samples from subjects that are symptomatic for the disease. Deviation between standard and subject values establishes the parameters for diagnosing the disease.

In another embodiment of the invention, the polynucleotides encoding HPLMH may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HPLMH may be implicated. The diagnostic assay may be used to distinguish between absence, presence, and excess expression of HPLMH, and to monitor regulation of HPLMH levels during therapeutic intervention.

In one aspect, hybridization or PCR probes which are capable of detecting polynucleotide sequences, including genomic sequences, encoding HPLMH or closely related molecules, may be used to identify nucleic acid sequences which encode HPLMH. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate or low) will determine whether the probe identifies only naturally occurring sequences encoding HPLMH, alleles or related sequences.

Probes may also be used for the detection of related sequences, and should preferably contain at least 50% of the nucleotides from any of those HPLMH encoding sequences. The hybridization probes of the subject invention may be derived from the nucleotide sequence of SEQ ID NO:2 or from genomic sequence including promoter, enhancer elements, and introns of the naturally occurring HPLMH.

Other means for producing specific hybridization probes for DNAs encoding HPLMH include the cloning of nucleic acid sequences encoding HPLMH or HPLMH derivatives into vectors for the production of RNA probes. Such vectors are known in the art, commercially available, and may be used to synthesize RNA probes in vitro by means of the addition of the appropriate RNA polymerase, such as T7 or SP6 RNA polymerase, and the appropriate radioactively labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding HPLMH may be used for the diagnosis of conditions or diseases which are associated with expression of HPLMH. Examples of such conditions or diseases include central nervous system diseases such as Alzheimer's disease, Parkinson's disease, Huntington's disease, Creutzfeld-Jacob disease, amyotrophic lateral sclerosis, and hydrocephalus, cardiovascular diseases such as angina, cardiac hypertrophy, congestive heart failure, vasoconstriction, and hypertension, prostate hypertrophy, disorders related to smooth muscle function such as bladder and sphincter dysfunction, bronchial constriction, and asthma. The polynucleotide sequences encoding HPLMH may be used in hybridization or PCR assays of fluids or tissues from patient biopsies to detect HPLMH expression. The form of such qualitative or quantitative methods may include Southern or northern analysis, dot blot, or other membrane-based technologies PCR technologies, dip stick, pin, chip, and ELISA, all methods which are well known in the art.

In order to provide a basis for the diagnosis of disease associated with expression of HPLMH, a normal or standard profile for expression is established. This may be accomplished by combining body fluids or cell extracts taken from normal subjects, either animal or human, with polynucleotides encoding HPLMH, or a fragment thereof, under conditions suitable for hybridization or amplification. Standard hybridization may be quantified by comparing the values obtained from normal subjects with a dilution series of polynucleotides encoding HPLMH measured in the same experiment, where a known amount of a substantially purified polynucleotides encoding HPLMH is used. Standard values obtained from normal samples may be compared with values obtained from samples from patients who are symptomatic for disease associated with HPLMH. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for oligonucleotides encoding HPLMH may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HPLMH include radiolabeling or biotinylating nucleotides, coamplification of a control nucleic acid, and standard curves onto which the experimental results are interpolated (Melby P. C. et al. (1993) J Immunol Methods, 159:235–244; Duplaa C. et al. (1993) Anal Biochem 229–236.) The speed of quantitation of multiple samples may be accelerated by running the assay in an ELISA format where the oligomer of interest is presented in various dilutions and a spectrophotometric or colorimetric response gives rapid quantitation.

In other embodiments of the invention, the nucleotide sequences of the invention may be used in molecular biology techniques that have not yet been developed, provided the new techniques rely on properties of nucleotide sequences that are currently known, such as the triplet genetic code, specific base pair interactions, and the like.

In another embodiment of the invention, the nucleic acid sequence which encodes HPLMH may also be used to generate hybridization probes which are useful for mapping the naturally occurring genomic sequence. The sequence may be mapped to a particular chromosome or to a specific region of the chromosome using well known techniques. Such techniques include in situ hybridization to chromosomal spreads, flow-sorted chromosomal preparations, or artificial chromosome constructions, such as yeast artificial chromosomes, bacterial artificial chromosomes, bacterial PI constructions or single chromosome cDNA libraries as reviewed in Price C. M. (1993) Blood Rev 7:127–134, and Trask B. J. (1991) Trends Genet 7:149–154.

The technique of fluorescent in situ hybridization of chromosome spreads, as described in Vera et al. (1988) *Human Chromosomes: A Manual of Basic Techniques*, Pergamon Press, New York, N.Y., may also be used. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding HPLMH on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HPLMH, its functional, catalytic or immunogenic fragments or oligopeptides thereof, can be used for screening libraries of compounds in any of a variety of drug screening techniques. The fragment employed in such a test may be free in solution, affixed to a solid support, borne on a cell surface, or located intracellularly. The formation of binding complexes, between HPLMH and the agent being tested, may be measured.

Another technique for drug screening which may be used provides for high throughput screening of compounds having suitable binding affinity to the protein of interest as described in published PCT application WO84/03564. In this method, as applied to HPLMH, large numbers of different small test compounds are synthesized on a solid substrate, such as plastic pins or some other surface. The test compounds are reacted with HPLMH, or fragments thereof, and washed. Bound HPLMH is then detected by methods well known in the art. Purified HPLMH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPLMH specifically compete with a test compound for binding to HPLMH. In this manner, the antibodies can be used to detect the presence of any peptide which shares one or more antigenic determinants with HPLMH.

In additional embodiments, the nucleotide sequences which encode HPLMH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I Construction of PROSNOT05 cDNA Library

The PROSNOT05 cDNA library was constructed from a non-tumorous prostate tissue removed from a 67-year-old Caucasian male (specimen #0036B; Mayo Clinic, Rochester, Minn.) by radical prostatectomy. The pathology report indicated Mayo grade 3 (of 4) adenocarcinoma (Gleason grade 3+3) in the periphery of the prostate. Perineural invasion was present as was involvement of periprostatic tissue. Non-tumorous portions of the prostate exhibited adenofibromatous hyperplasia. The patient had elevated levels of prostate specific antigen (PSA). Pelvic lymph nodes were negative for tumor. A prior stomach ulcer and atherosclerosis were reported in the patient history; however, the patient was not on any medication at the time of surgery.

The frozen tissue was homogenized and lysed using a Brinkmann Homogenizer Polytron-PT 3000 (Brinkmann Instruments, Inc., Westbury, N.Y.) in guanidinium isothiocyanate solution. The lysate was extracted once with acid phenol at pH 4.0 per Stratagene's RNA isolation protocol (Stratagene Inc., San Diego, Calif.). The lysate was reextracted once more with phenol chloroform at pH 4.0. The RNA was then precipitated using 0.3M sodium acetate and 2.5 volumes of ethanol, resuspended in DEPC-treated water and DNase treated for 25 min at 37° C. The RNA was again extracted once with an equal volume of acid phenol, and reprecipitated using conditions described above. The mRNA was isolated using the Qiagen Oligotex kit (QIAGEN Inc., Chatsworth, Calif.) and used to construct the cDNA library.

The RNA was handled according to the recommended protocols in the SuperScript Plasmid System for cDNA Synthesis and Plasmid Cloning (catalog #18248–013; Gibco BRL). cDNAs were fractionated on a Sepharose CL4B column (catalog #275105, Pharmacia), and those cDNAs exceeding 400 bp were ligated into pSport I. The plasmid pSport I was subsequently transformed into DH5a™ competent cells (Cat. #18258-012, Gibco B.L.).

II Isolation and Sequencing of cDNA Clones Plasmid DNA was released from the cells and purified using the REAL Prep 96 Plasmid Kit for Rapid Extraction Alkaline Lysis Plasmid Minipreps (Cat. #26173). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) the cultures were incubated for 19 hours after the wells were inoculated and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage.

The cDNAs were sequenced by the method of Sanger F. and Coulson A. R. (1975; J Mol Biol 94:441f), using a Hamilton Micro Lab 2200 (Hamilton, Reno, Nev.) in combination with Peltier Thermal Cyclers (PTC200 from MJ Research, Watertown, Ma.) and Applied Biosystems 377 DNA Sequencing Systems; and the reading frame was determined.

III Homology Searching of CDNA Clones and Their Deduced Proteins

Each cDNA was compared to sequences in GenBank using a search algorithm developed by Applied Biosystems and incorporated into the INHERIT™670 Sequence Analysis System. In this algorithm, Pattern Specification Language (TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 Sequence Analysis System using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul et al. (1990) J Mol Biol 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for homology between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul S. F. 1993 and 1990, supra) are used to search for identical or related molecules in nucleotide databases such as GenBank or the LIFESEQ™ database (Incyte Pharmaceuticals, Inc., Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ seqence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of HPLMH-Encoding Polynucleotides to Full Length or to Recover Regulatory Elements Full length HPLMH-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers are used to facilitate the extension of the known HPLMH-encoding sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Ma.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 15 sec                        |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and cut out of the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μof ligation buffer, 1 μl T4-DNA ligase (15 units) and 1 μl T4 polynucleotide kinase are added, and the mixture is incubated at room temperature for 2–3 hours or overnight at 16° C . Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec                           |
|--------|---------------------------------------------|
| Step 2 | 94° C. for 20 sec                           |
| Step 3 | 55° C. for 30 sec                           |
| Step 4 | 72° C. for 90 sec                           |
| Step 5 | Repeat steps 2–4 for an additional 29 cycles|
| Step 6 | 72° C. for 180 sec                          |
| Step 7 | 4° C. (and holding)                         |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham, Chicago, Ill.) and T4 polynucleotide kinase (DuPont NEN®, Boston, Ma.). The labeled oligonucleotides are substantially purified with Sephadex G-25 superfine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1 or Pvu II; DuPont NEN®).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The HPLMH-encoding sequence, or any part thereof, is used to inhibit in vivo or in vitro expression of naturally occurring HPLMH. Although use of antisense oligonucleotides, comprising about 20 base-pairs, is specifically described, essentially the same procedure is used with larger cDNA fragments. An oligonucleotide based on the coding sequences of HPLMH, as shown in FIG. 1, is used to inhibit expression of naturally occurring HPLMH. The complementary oligonucleotide is designed from the most unique 5' sequence as shown in FIG. 1 and used either to inhibit transcription, by binding to the DNA near the transcription initiation site, or translation of an HPLMH-encoding transcript by preventing the ribosome from binding to the 5' untranslated region. Using an appropriate portion of the 5' sequence of SEQ ID NO:2, an effective antisense oligonucleotide includes any 15–20 nucleotides spanning the region which is translated into the amino terminus of the polypeptide as shown in FIGS. 1 and 2.

VIII Expression of HPLMH

Expression of the HPLMH is accomplished by subcloning the cDNAs into appropriate vectors and transforming the vectors into host cells. In this case, the cloning vector, pSport, previously used for the generation of the cDNA library is used to express HPLMH in E. coli. Upstream of the cloning site, this vector contains a promoter for β-galactosidase, followed by sequence containing the amino-terminal Met, and the subsequent seven residues of B3-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first seven residues of β-galactosidase, about 5 to 15 residues of linker, and the full length HPLMH-encoding sequence. The signal sequence directs the secretion of HPLMH into the bacterial growth media which can be used directly in the following assay for activity.

IX Demonstration of HPLMH Activity

The channel-forming ability of HPLMH is assayed by monitoring efflux of Cl$^-$ ions from vesicles containing HPLMH and subjected to a transmembrane ion potential. HPLMH and mitochondrial cytochrome C oxidase, a proton pump, are reconstituted into lipid vesicles by sonication. $^{36}$Cl$^-$ is then incorporated into the vesicles by passive diffusion, incubating the vesicles in a solution containing [$^{36}$Cl]-potassium chloride for several hours. The vesicles are then dispersed in an appropriate reaction buffer. Addition of ascorbate and cytochrome C initiates proton uptake into the vesicles generating an interior-positive membrane potential. The voltage generated across the membrane activates gating of the HPLMH ion channel. At predetermined times, aliquots of the vesicle-containing solution are removed from the reaction buffer and filtered through 0.2 mμ membrane filters (Millipore, Marlborough, Ma.). The vesicles are retained on the filters. The filters are rinsed and dried. Radioactivity on the filters is measured in a scintillation counter. The decrease in radioactivity on the filters as a function of reaction time gives a measure of the rate of Cl$^-$ efflux through the voltage-activated HPLMH ion channel.

Alternatively, Xenopus oocytes are microinjected with RNA, corresponding to the message sequence encoding HPLMH which can be synthesized in vitro by techniques well known to those skilled in the art. Oocytes injected with HPLMH RNA are compared with mock-injected oocytes for [$^3$H]taurine fluxes as described in detail (Moorman J. R. et al., supra).

A third method is to measure currents regulated or modulated by HPLMH directly by introducing in vitro expressed HPLMH protein into synthetic phospholipid bilayers and measuring ion flux using standard electrophysiological techniques well known to those versed in the art. Alternatively, ion currents can be measured electrophysiologically in Xenopus oocytes that are microinjected with in vitro synthesized HPLMH RNA using techniques well known in the art.

X Production of HPLMH Specific Antibodies

HPLMH that is substantially purified using PAGE electrophoresis (Sambrook, supra), or other purification techniques, is used to immunize rabbits and to produce antibodies using standard protocols. The amino acid sequence translated from HPLMH is analyzed using DNASTAR software (DNASTAR Inc.) to determine regions of high immunogenicity and a corresponding oligopolypeptide is synthesized and used to raise antibodies by means known to those of skill in the art. Analysis, such as that described by Ausubel et al. (supra), may be used to select appropriate epitopes, such as those near the C-terminus or in hydrophilic regions.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPLMH Using Specific Antibodies

Naturally occurring or recombinant HPLMH is substantially purified by immunoaffinity chromatography using antibodies specific for HPLMH. An immunoaffinity column is constructed by covalently coupling HPLMH antibody to an activated chromatographic resin, such as CnBr-activated Sepharose (Pharmacia Biotech). After the coupling, the resin is blocked and washed according to the manufacturer's instructions.

Media containing HPLMH is passed over the immunoaffinity column, and the column is washed under conditions that allow the preferential absorbance of HPLMH (e.g., high ionic strength buffers in the presence of detergent). The column is eluted under conditions that disrupt antibody/HPLMH binding (e.g., a buffer of pH 2–3 or a high concentration of a chaotrope, such as urea or thiocyanate ion), and HPLMH is collected.

XII Identification of Molecules Which Interact with HPLMH

HPLMH, or biologically active fragments thereof, is labeled with $^{125}$I Bolton-Hunter reagent (Bolton et al. (1973) Biochem J 133:529). Candidate molecules previously arrayed in the wells of a multi-well plate are incubated with the labeled HPLMH, washed and any wells with labeled HPLMH complex are assayed. Data obtained using different concentrations of HPLMH are used to calculate values for the number, affinity, and association of HPLMH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide consisting of SEQ ID NO:2.

2. An isolated and purified polynucleotide having a sequence which is completely complementary to SEQ ID NO:2.

3. A hybridization probe comprising the polynucleotide of claim 2.

4. An expression vector containing the polynucleotide of claim 1.

5. A host cell containing the expression vector of claim 4.

6. A method for producing a polypeptide comprising the amino acid sequence of SEQ ID NO:1, the method comprising the steps of:
   a) culturing the host cell of claim 5 under conditions suitable for the expression of the polypeptide; and
   b) recovering the polypeptide from the host cell culture.

7. A method for detecting a polynucleotide encoding a polypeptide comprising the amino acid sequence of SEQ ID NO:1 in a biological sample containing nucleic acid material, the method comprising the steps of:
   a) hybridizing a polynucleotide having a sequence which is completely complementary to SEQ ID NO:2 to the nucleic acid material of the biological sample, thereby forming a hybridization complex; and
   b) detecting the hybridization complex, wherein the presence of the hybridization complex is indicative of presence of a polynucleotide encoding a polypeptide comprising the amino acid sequence of SEQ ID NO:1 in the biological sample.

8. The method of claim 7 wherein the nucleic acid material of the biological sample is amplified by the polymerase chain reaction before the hybridizing step.

* * * * *